Aug. 6, 1968 C. F. ZAIGER Plant Pat. 2,826
APRICOT TREE
Filed Sept. 21, 1966
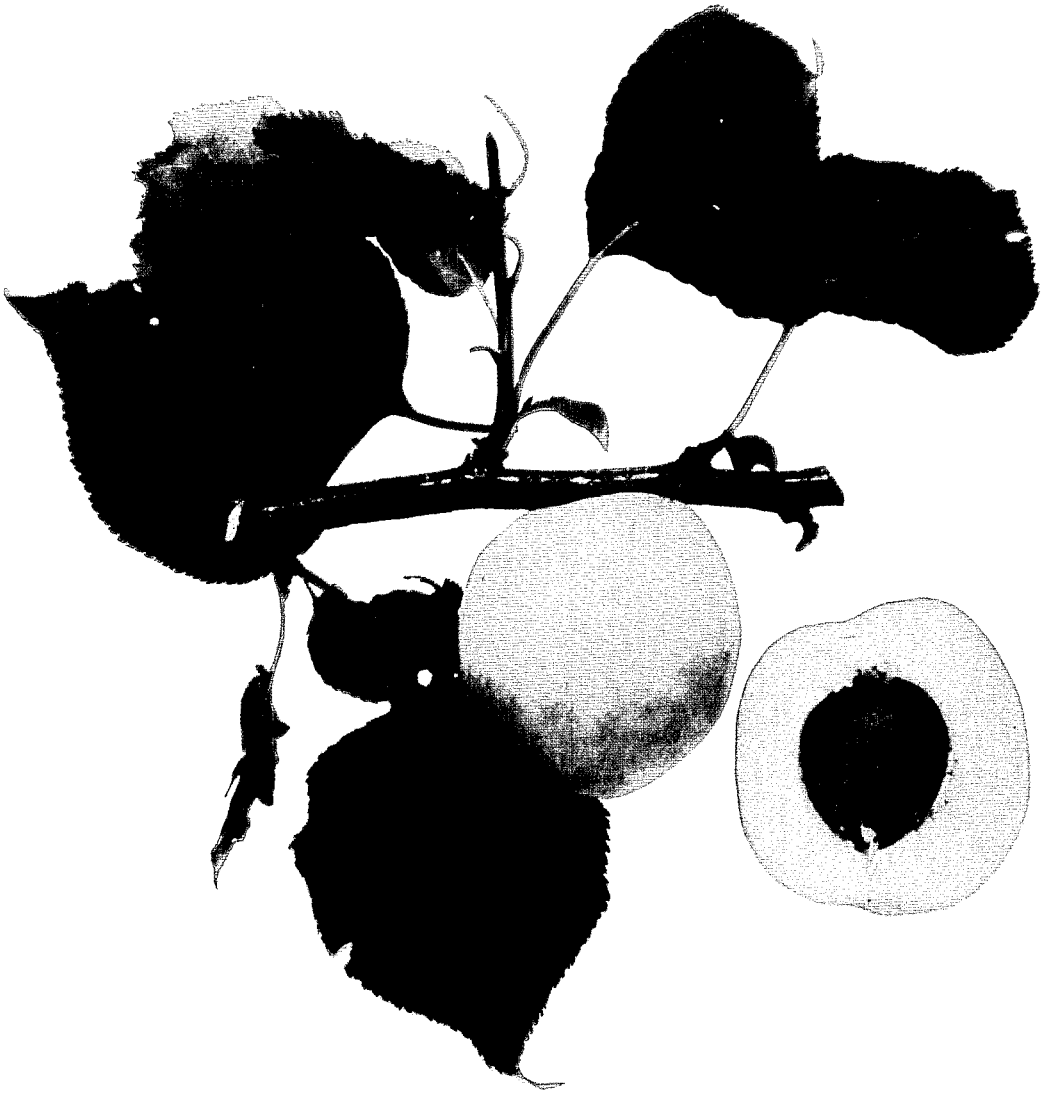
INVENTOR
C. Floyd Zaiger United States Patent Office Plant Pat. 2,826
Patented Aug. 6, 1968

2,826
APRICOT TREE

Chris Floyd Zaiger, 537 Rosemore Ave.,
Modesto, Calif. 95351

Filed Sept. 21, 1966, Ser. No. 581,427
1 Claim. (Cl. Plt.—39)

The present invention relates to a new and distinct variety of apricot tree. My new variety originated as a first generation seedling from a group of Perfection apricot (non-patented) seedlings grown by me on my property in Modesto, Calif. The pollen parent was of unknown origin.

Its novelty consists of the following unique combination of features which are outstanding in a new variety:

(1) The medium to large size of the fruit;
(2) A high degree of red skin color;
(3) The coloring of the fruit two to four weeks before ripening;
(4) The early ripening period of the fruit, occurring in late May;
(5) The heavy and consistent setting of fruit each year; and
(6) More even and uniform distribution of fruit on the tree.

In comparison to the seed parent, my new variety bears heavier and more consistently each year, has a higher degree of red skin color, and is much firmer, thus having greater shipping quality.

The foregoing characteristics and distinctions definitely differentiate my new variety from its seed parent, as well as from all other varieties of which I am aware, and a sexual reproduction of the new variety by budding and grafting, as performed at Modesto, Calif., shows that said characteristics come true to form and are established and transmitted through succeeding propagations.

The accompanying photographs show typical specimens of the foliage and fruit of my new variety, with upper and lower surfaces of the foliage being illustrated and exterior and a sectional view of the fruit being shown. These illustrations were taken shortly after being picked at maturity (shipping ripe). The colors are as nearly true as is reasonably possible in color representation of this type.

The following is a detailed description of the foliage and fruit of my new variety, as based upon observation of specimens grown at Modesto, Calif. with color terminology in accordance with Reinhold Color Atlas by A. Kornerup and J. H. Wanscher.

Dates of first and last picking: Generally ripens in late May, although over prolonged observations dates of first ripening varied from May 18 to May 28, with last picking from May 30 to June 9.

Tree:
*Size.*—Large to medium, vigorous, upright, dense.
*Figure.*—Usual.
*Shape.*—Usual.
*Productivity.*—Very heavy; regular bearer.

Branches: Vigorous, stocky to medium caliper in relation to length, from smooth to medium roughness.
*Color.*—Brown, Plate 6E6, to light brown, Plate 6D6.
*Lenticels.*—*Numerous, medium.*

Leaves:
*Size.*—Medium to large.
*Length.*—Averages 3½".
*Width.*—Averages 3".
*Form.*—Ovate to orbicular; abrupty pointed; medium thickness, relatively smooth.
*Margin.*—Coarsely serrate.
*Petiole.*—Average length, 1½". Average thickness, 3/32".
*Glands.*—Number, two to six. Size, medium. Positioned on petiole below attachment of leaf blade.
*Color.*—Upper surface dark green, 28F8. Lower surface grayish-green, 29E5.

Flower buds: Hardy.
*Size.*—Medium to small.
*Shape.*—Medium to short, pubescent.

Flowers:
*Date of blooms.*—Feb. 21, 1966, to Mar. 8, 1966; varies due to weather variations.
*Size.*—Medium to large.
*Color.*—Varies from white to light pink.
*Pubescent.*—Present.

Fruit:
*Shipping ripe.*—The third week of May.
*Eating ripe.*—The last week of May.
*Size.*—Medium to large. Axial diameter—from one and three-quarters inches to two and one-fourth inches. Transverse diameter in suture plane—from two inches to two and one-half inches. Diameter measured at right angles to suture plane—from two inches to two and one-quarter inches.
*Suture.*—Usually pronounced from stem to blossom end. Shallower near blossom end, terminates at blossom end.
*Form.*—Slightly variable, symmetrical, globose, somewhat compressed at suture.
*Cavity.*—From round to somewhat elongated in suture plane, with suture showing on one side. Depth—from about one-eighth (⅛) inch to three-sixteenth (3/16) inch. Breadth—about one-fourth (¼) inch.
*Base.*—Rounded.
*Apex.*—Rounded to slightly depressed; with pistil point slightly depressed.

Skin: Thin, tender, tenacious to flesh, slight tendency to crack.
*Color.*—Reddish-orange, Plate 7B7, to light yellow, Plate 4A5, at maturity the fruit is usually bright and colorful.
*Down.*—Scant, very short.

Flesh:
*Color.*—Between orange, Plate 5A7, to light orange, Plate 5A5.
*Amygdalin.*—Scant.
*Juice.*—Moderate.
*Fibres.*—Medium size; tender.
*Ripens.*—Fairly even; slightly earlier at apex.
*Flavor.*—Mild; delicate.
*Eating quality.*—Good.

Stones:
*Type.*—Free, adheres to flesh somewhat along ventral edge.
*Fibres.*—Some adherent.
*Size.*—Approximately one inch long, fifteen-sixteenths of an inch wide, and one-half in transversely of the suture plane.
*Form.*—Ovid; very slightly cunate toward apex.
*Base.*—Straight.
*Hilium.*—Oval.
*Apex.*—Nearly rounded.
*Surface.*—Regularly pitted, only slightly throughout.
*Ridges.*—Sharp ridges only along ventral edge.
*Tendency to split.*—None.
*Color.*—From brownish-orange, Plate 5C6, to yellowing brown, Plate 5D5.

Use: Canning, freezing, drying, and fresh for shipping and local market.
Keeping quality: Good.
Shipping quality: Good.

I claim:

A new and distinct variety of apricot tree, substantially as herein shown and described, characterized particularly as to novelty by its medium to large fruit, the relatively high red skin color on the side of the fruit exposed to the sun, its shorter maturation period than "Perfection" apricot, and its earlier ripening habit ranging from three to four weeks ahead of "Perfection" apricot in Modesto, Calif.

No references cited.

ROBERT E. BAGWILL, *Primary Examiner.*